(12) United States Patent
Rondelez et al.

(10) Patent No.: US 6,316,015 B1
(45) Date of Patent: Nov. 13, 2001

(54) HYPERBACTERICIDAL SURFACES

(75) Inventors: Francis Rondelez, Fontenay aux Roses; Pascal Bezou, Paris; Othman Bouloussa, Gradignan, all of (FR)

(73) Assignees: Institut Curie; Centre National de la Recherche Scientifique, both of Paris Cedex (FR)

( * ) Notice: Subject to any disclaimer, the term of this patent is extended or adjusted under 35 U.S.C. 154(b) by 0 days.

(21) Appl. No.: 09/240,626

(22) Filed: Feb. 1, 1999

Related U.S. Application Data

(63) Continuation of application No. PCT/FR97/01403, filed on Jul. 25, 1997.

(30) Foreign Application Priority Data

Jul. 31, 1996 (FR) .................................................. 96 09677

(51) Int. Cl.[7] .................................................. A01N 25/22
(52) U.S. Cl. .......................... 424/409; 424/405; 514/197; 514/198; 514/199; 514/200; 514/642; 514/643
(58) Field of Search ..................................... 424/405, 409; 514/197–207, 642, 643; 523/122

(56) References Cited

U.S. PATENT DOCUMENTS 5,104,649  4/1992  Jansson et al. .
5,490,938 *  2/1996  Sawan et al. ........................ 210/651

FOREIGN PATENT DOCUMENTS 0 328 421  8/1989  (EP) .
WO 80/02840  12/1980  (WO) .
WO 89/05616  6/1989  (WO) .

\* cited by examiner

*Primary Examiner*—Neil S. Levy
(74) *Attorney, Agent, or Firm*—Young & Thompson

(57) ABSTRACT

A surface is provided with antibiotic or antiseptic properties. A solid substrate is modified by covalently fixing one or more spacers having reactive extremities via a proximate reactive extremity, and one or more antibiotic, bactericidal, viricidal or fungicidal molecules covalently bonded to a distal reactive extremity of the spacer or spacers. The spacer has formula $$A_1\text{—}(CH_2)_n\text{—}A_2,$$

where:

$A_1$ is

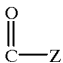

where Z=H, OH or Cl; or $SiY_3$ where $Y_3$ is Cl or an alkoxy group containing 1 to 3 carbon atoms;

n is in the range 2 to 18;

$A_2$ is selected from the following residues: $CH=CH_2$, OH, halogen or

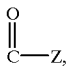

where Z=H, OH or Cl.

6 Claims, No Drawings

HYPERBACTERICIDAL SURFACES

This application is a continuation of international application PCT/FR97/01403 filed Jul. 25, 1997, which designated the United States.

The present invention relates to a process for producing a surface with permanent antibiotic, bactericidal, fungicidal or viricidal properties, to surfaces which can be obtained by the production process, and to their use in the medical, cosmetics, food, hygiene or industrial fluids industries.

Throughout the present text, the terms "antibiotic", "cytotoxic", "bactericidal" molecules or substances should be deemed to include not only the bactericidal property itself, but also a viricidal, fungicidal or in general any bio-active substance which is cytotoxic to any living cell the elimination of which is desired.

Bactericidal surfaces already exist, in particular for medical use, for example gloves or fabrics. Non covalent mixtures of the surfaces and bactericidal substances have been described; a particular example is a pair of gloves incorporating a liquid medium containing an effective pharmacological agent between two layers of latex (French patent 87 11753); a further example is an emulsion of micro-droplets stabilised by a block copolymer (French patent number 93 15561, dated Dec. 23, 1993).

Medical implants or catheters have also been coated with an antibiotic or a mixture of antibiotics; the bonding with the support is ionic and the antibiotic is simply adsorbed on the substrate (International patent application WO 93 17746).

European patent EP-A-0 348 462 describes contact lenses constituted by an acrylic polymer the surface of which is modified by grafting organic molecules with the desired properties (UV resistance, selective cytotoxicity, etc . . . ). This molecule comprises a silane group which is reactive towards the carboxyl groups of the acrylic polymer chains. The modified surface of such lenses comprises a multilayer of the selected chemical group with a range of thicknesses: 50 to 100 Å in some cases (Table 1, column 4), 2000 to 6000 Å in other cases when the lens is modified to endow it with particular properties.

Depositing organic molecules on glass or silica substrates by grafting a monolayer has been described in Appl. Phys. Lett., 62, 2256 (1993), Sciences et Avenir, 567, 87 (1994) and in La Recherche, 275 (26), 460 (1995); applications for such modified surfaces are in the fields of self-lubricating surfaces, ultra-thin electrical insulators and stay-clean windows.

Antibiotic surfaces are of particular importance in the battle against the development of nosocomial infections in a hospital environment; the availability of materials the surface of which are cytotoxic and which could inhibit the development of bacteria which come into contact with those materials would be of great interest. These would include surgical instruments, catheters, and also crockery, doors and windows, wall coverings, ceramics etc . . . Further, the appearance of bacterial strains which have become resistant to normal doses of antibiotics necessitates the use of ever increasing concentrations of cytotoxic products. Thus the number of antibiotic molecules per unit surface area must be as high as possible.

The present invention provides a surface endowed with antibiotic, antiseptic, viricidal or fungicidal properties constituted by a mineral or organic solid substrate, the surface of which has been coated, using suitable chemical means, with a homogeneous, dense monolayer of molecules with these bio-active properties. Said molecules are fixed to the substrate by covalent bonds, which endows the active layer with a permanent and irreversible character.

The modified substrate of the invention is characterized in that the antibiotic molecules are fixed to the surface by covalent bonds via one or more "spacers".

The spacer molecules are generally alkyl chains, composed of a series of 2 to 18 carbon atoms, and with functional groups at each extremity to enable an irreversible covalent bond to be formed firstly with a surface site of the solid substrate, and secondly with the bio-active molecule.

The spacer of the invention preferably has the formula

where:

$A_1$ is

where Z=H, OH or Cl; or $SiY_3$ where $Y_3$ is Cl or an alkoxy group containing 1 to 3 carbon atoms;

the number n of methylene groups forming the alkyl chain is in the range 2 to 24;

$A_2$ is selected from the following residues: $CH_3$, $CH=CH_2$, OH, halogen or

where Z=H, OH or Cl.

In the above formula, n is preferably in the range 5 to 18. Too short a spacer would run the risk of too high a rigidity while if it were too long, there would be a risk of the aliphatic chain folding back on itself, which would lead to less effective coupling with the antibiotic.

The substrates to be modified are either mineral surfaces, in particular silica based (sand, glass beads, glass wool), or organic substrates, depending on the desired use in fields as disparate as those cited above. Non limiting examples of organic substrates are polyethylene, polyvinyl chloride (PVC), polyacrylates, polymethacrylates, polypropylene, polyamides, polyurethanes, acrylonitrile-butadiene-styrene (ABS), saturated or unsaturated polyesters such as polyethylene terephthalate (PET), polycarbonates, polyacrylamides, Teflon® (PTFE), polysiloxanes, polysaccharides or any polymer or copolymer which can be grafted with a spacer containing two reactive extremities. The substrate can also be a metal or its oxide such as aluminium (Al), tin (Sn) or indium (In).

Some of the substrates used, in particular organic substrates, contain naturally reactive functions, either in their side chains such as PVC (Cl), polyacrylate (—COOH), polyamide (—CO—$NH_2$) or polyhydroxymethylsiloxane (Si—H), or in their main chain such as polyurethane (—NH—CO—O—), polycarbonate (—O—CO—O—), or polyesters (—CO—O—).

In other compounds, however, the reactive functions have to be generated in situ using standard activation methods such as chemical oxidation or plasma treatment, using techniques described by L. Penn et al., ("Polymers for Advanced Technologies" (1994), 5: 809–817); this is the case, for example, for polyethylene and for numerous other polymers or copolymers.

In addition to the polymers cited above, any polymer containing reactive groups in its framework, or at its surface, or containing groups which can be transformed into a reactive group, are good candidates as a substrate for the surfaces of the invention. The surface is, of course, selected depending on the antibiotic or cytotoxic use which it is desired to develop.

The shapes of the surfaces can also vary depending on the desired use.

In biological or medical fields, flat or almost flat surfaces are encountered in bottles, pouches, flasks or other components; they can be tubular surfaces such as in catheters, syringes, needles, etc . . . ; or in hollow or solid microfibres. Hollow microfibres are used, for example, in renal dialysis cartridges or in hollow fibre systems for culturing animal cells.

Spherical surfaces are encountered in beads or microbeads and can have any diameter which is appropriate for the desired use, in particular between a few microns and several millimetres. Examples of the use of beads are in children's sandpits, in the abrasive contained in toothpaste, and in systems for purifying water by contact with particles with a high specific surface area to decontaminate a solution by simple stirring with no risk of releasing the antibiotics into the medium.

When decontaminating industrial fluids (cutting fluid for machine tools, etc . . . ), the surfaces can be solid fibres assembled into a filtering cartridge.

Antibiotics which can be used for producing the surfaces of the invention are necessarily antibiotics which preferably act on the cell wall; antibiotics which act on a transcription or translation level are of less interest in the present case since covalent fixing does not allow the antibiotic to penetrate into the bacterium under the conditions which subsist when in solution.

In particular, these antibiotics can be those containing a β-lactam nucleus such as penicillins, cephalosporins, monobactams, thienamycins, β-lactamase inhibitors, peptidoglycan synthesis inhibitors, or basic polypeptides such as bacitracin or novobiocin.

Quaternary ammonium based bactericides and fungicides selected from:

the imidazoles, such as nystatin and amphotericin B;

aliphatic fungicides such as zinc, calcium or sodium undecylenate;

carbamates, dithiocarbamates and iodocarbamates such as 3-iodo-2-butyl carbamate;

organomercury derivatives such as methoxy-ethyl-mercury silicate;

heterocyclic fungicides such as triazines or 1,3,5-hexahydrotriazine;

isothiazoline, pyridine ethione, aminated alcohol derivatives, etc . . . can also form part of the constitution of the active surfaces of the invention.

The bactericide or antibiotic may necessitate prior chemical modification to enable it to graft to a surface, for example a glass surface. To this end, the reactive groups in the antibiotics are used, such as the amine group naturally present in the chemical structure of some antibiotics comprising a β-lactam nucleus such as aminopenicillanic acid.

The antibiotic molecules form a monolayer, with a thickness of less than 4 nm, on the modified substrate of the invention.

The layer can be homogeneous or heterogeneous in its composition in order to optimise the antibiotic, fungicidal or viricidal properties and if necessary to broaden the antibiotic spectrum of the modified surface; the heterogeneity can be on a molecular level or on a macroscopic level: as an example, microbeads, which are individually homogeneous and carry molecules of different natures, can be mixed together.

Depending on the antibiotic spectrum with which it is desired to endow the surface of the invention, the skilled person will know whether it is necessary to graft a single antibiotic and which it will be, or whether a mixture of a plurality of antibiotics has to be grafted and in which proportions. In the second case, either a single type of spacer can be used and the selected antibiotics react with the same reactive extremity of the spacer, or a plurality of spacer types can be used, each being capable of reacting with a particular antibiotic. It is also possible to mix molecules with different bio-active specificities.

The monolayer formed by the bio-active molecules is very dense and the molecules are in direct contact with each other, forming a compact two-dimensional array.

The antibiotic active site density per surface area unit for the surfaces of the invention can be as high as $5 \times 10^4$ molecules of antibiotics per square centimeter. This density leads to a very high local concentration of about 1 mole per litre or 400 g/l, i.e., more than ten thousand times higher than the usual concentration in volumetric solution, which renders the cytotoxic efficacy of this surface extremely high and the risk of development of resistant strains becomes substantially zero.

If desired, and for particular applications, it is possible to reduce the density of bio-active molecules present on the surface of the material by introducing a variable concentration of passive spacers, i.e., which are incapable of forming a covalent bond with a bio-active molecule. The density of the antibiotics can thus be readily adjusted, for example between $10^{11}$ and $5 \times 10^{14}$ molecules/cm$^2$.

Risks of accidental release of cytotoxic molecules into the external medium, and from the surface, do not exist. The monolayer is irreversibly grafted onto the solid substrate. The bio-active molecules thus cannot become detached from the substrate onto which they have been fixed. The covalent bonds with the substrate and between the molecules themselves inside the monolayer are extremely strong and can only be destroyed by very particular chemical or photochemical treatments (ultraviolet irradiation at about 210 nm in the presence of ozone, ionising radiation, etc . . . ). Further, even if the complete layer becomes detached, the biological risks remain limited: if 1 cm$^2$ of the grafted layer is dissolved in a 1 ml volume of liquid, for example, blood, the antibiotic concentration will be a maximum of 1 μmole/litre, or 0.4 mg/litre. There is thus a considerable dilution effect. Compared with the local concentration present on the surface of the cytotoxic material, the dilution ratio is $10^6$. A concentration of 1 μmole/litre is not at all dangerous to the organism.

The materials with cytotoxic properties described in this invention can thus be used for subcutaneous, intramuscular or intravascular applications.

The monolayer resists long-term cleaning with aqueous or organic solvents, even at temperatures of the order of 120° C.

The monolayer is permanent and does not require particular storage and preservation conditions.

The present invention also encompasses a process for covalently fixing molecules with a bactericidal or antibiotic nature onto organic and mineral surfaces by means of spacer type molecules with the formula given above. This process is different depending on the exact nature of the support and of the antibiotic to be grafted.

When the surface is glass or silica, this process for preparing surfaces has already been described in the particular case where the grafted molecules are trichloroalkyl-silanes or trialkoxyalkylsilanes which do not comprise a functional group at its free extremity enabling covalent bonding with an antibiotic molecule (Nature, 360, 719 (1992)). A detailed description of the method used to deposit a monolayer of hydrocarbon-containing chains onto hydrated silica surfaces via a trichlorosilane group can be found in a number of recent articles (J. B. Brzoska et al., (1994) Langmuir 10: 4367–4373; D. L. Allara et al., (1995), Langmuir 11: 2357, 2360).

The process described in those articles was significantly modified to enable bio-active molecules to be fixed.

The surface preparation process thus comprises:

pre-cleaning said surface, the aim of the cleaning being to eliminate any particle or molecule which could prevent the spacer from affixing to the reactant groups of the surface;

if necessary, chemically activating the solid surface to generate reactive groups;

depositing a capture layer with a reactive function at the outer terminal position;

chemically grafting the antibiotic or bactericide onto the reactive group on the modified surface.

When the surfaces are mineral surfaces, cleaning is carried out:

either by immersion in a 15% hydrogen peroxide ($H_2O_2$) solution which is decomposed by adding a few drops of $FeCl_3$, followed by a second immersion in a solution of 50% $H_2SO_4$;

or by immersion in a bath of 15% hydrogen peroxide and sodium hydroxide (12 g/l).

The reactivity of these surfaces can be increased by immersing them in a 3% to 10% HF solution for a few seconds.

The treated surfaces are then rinsed with copious quantities of distilled water and oven dried at 80° C. for 10 to 15 minutes.

When the surfaces are organic, it may be necessary to generate reactive groups, depending on the nature of the support:

a) if the substrate is PVC, the surface is first activated by the following treatment:

contact with an aqueous $10^{-2}$ mol/l sodium azide solution for 24 hours, at 20–45° C.;

rinsing with water;

contact with an aqueous $10^{-2}$ mol/l $NaBH_4$ solution for 24 hours, at 20–45° C.

c) when the substrate is polyethylene terephthalate (PET), the surface is first activated by bringing the surface into contact with a 1% to 5% solution of 3-aminopropyltriethoxysilane in toluene for 24 hours in argon.

In general, whether the substrate is naturally reactive or modified to render it reactive, the process of the invention consists of reacting the reactive groups on the surface of the solid substrate with "spacer" molecules comprising a head which can be grafted to the support, an alkyl chain containing 2 to 18 methyl groups and an outer terminal function which grafts the bio-active molecule. As an example, 11-(trichlorosilyl)undeconyl chloride (TCSUC) can be used. The pre-cleaned support, which may have been activated, is immersed in a solution containing "spacer" molecules (about $10^{-3}$ M). The reaction is carried out for 24 hours at room temperature.

The bio-active molecules used can either be quaternary ammonium compounds such as 2-hydroxyethyldimethyldodecylammonium bromide (HEDMDA), or antibiotics such as triethylammonium 6-aminopenicillanate (APATEA), or fungicides.

In general, these molecules must contain a functional group which enables a covalent bond to be formed with the "spacer" molecules deposited on the substrate.

The reaction is carried out by immersing the solid support modified with "spacer" molecules in a dilute solution containing the antibiotic (about $10^{-3}$ M). The reaction takes 24 hours at room temperature.

The present invention also encompasses the use of the surfaces of the invention described above, and which can be obtained by the process described above and illustrated in the following examples.

The use of the surfaces of the invention for decontamination purposes may be of interest to a number of industrial fields, such as the health, hygiene and agro-alimentary industries. Examples are:

using a surface for the production of containers for medical use, such as bottles, pouches, or tubes, in particular disposables;

using a surface for the production of medical apparatus for ex vivo or in vivo organ treatment, such as renal dialysis cartridges;

using a surface for the production of materials or equipment for dentistry or for cleaning teeth;

using a surface for the production of osseous or vascular prostheses;

using a surface for decontaminating domestic fluids, in particular water and beverages (fruit juices, milk, wine, etc . . . ), or other fluid foodstuffs;

using a surface for decontaminating industrial fluids and effluents, for example cutting fluid, lubricants or petroleum fluids such as gas oil, gasoline or kerosine.

The following non limiting examples are intended to illustrate the preparation of the surfaces of the invention and their bactericidal properties, as a function of the support used, the antibiotic which is grafted, and the nature of the bacteria which are to be destroyed.

EXPERIMENTAL SECTION

All surfaces were characterized by infrared (IR), photo-spectroscopy (XPS), ellipsometry and measurement of the contact angle using the sessile drop method described by C. Allain et al., Journal of Colloid and Interface Science, 107, 5 (1985).

I. Preparation of Reactants

By way of example, a silane carrying a vinyl terminal group, a silane carrying an acid chloride terminal group, a penicillanic antibiotic and two bactericides were used. The preparation of the latter three compounds is described below.

Ia. 11-(trichlorosilyl)undecenoyl chloride (TCSUC)

5 ml (50 μmole) of trichlorosilane, 3.6 ml (17 μmole) of undecenoyl chloride and 220 mg of re-crystallised AIBN (2.2'-azo-bis-isobutyronitrile) were introduced into a flask. After degassing, the flask was sealed under vacuum and heated to 80° C. for 36 hours. The reaction product was distilled under vacuum ($T_d$=128° C., 0.2 mm Hg). Yield: 50%.

Ib. Triethylammonium 6-aminopenicillinate (APATEA)

2 g (10 μmole) of 6-aminopenicillanic acid (6-APA) was suspended in 60 ml of an $EtOH/H_2O$ mixture (5/1, v/v), and 1.4 ml (10 μmole) of triethylamine (TEA) was added. After dissolving completely, the solvent was evaporated off and the product was vacuum dried. Yield: 100%.

Ic. 2-Hydroxyethyl-Dimethyldodecylammonium Bromide (HEDMDA)

10 g (47 µmole) of N,N-dimethyldodecylamine and 10 g (80 µmole) of 2-bromoethanol were dissolved in 60 ml of acetone. The mixture was stirred under reflux for 6 hours. After cooling, the HEDMDA precipitated out. The precipitate was filtered, washed with ether and vacuum dried. Yield: 81%.

5-bromopentyl-dimethyldodecylammonium bromide (BPDMDA) was prepared using the same procedure, using 1,5-dibromopentane instead of 2-bromoethanol.

II. Preparation of Mineral Surfaces

IIa. Cleaning Surfaces

Two cleaning methods were used:
1. The surfaces were immersed in a 15% $H_2O_2$ solution for 30 to 60 minutes, the $H_2O_2$ being decomposed by adding a few drops of $FeCl_3$. They were then soaked for 5 minutes in a 50% $H_2SO_4$ solution, rinsed with copious quantities of distilled water and oven dried at 80° C. for 10–15 minutes.
2. The surfaces were immersed in a 15% $H_2O_2$ solution. Powdered sodium hydroxide (12 g/l) was carefully added and stirring was carried out for 1 hour. After rinsing with water, the surfaces were oven dried at 80° C. for 10–15 minutes.

IIb. Deposit of the Capture Layer with an Acid Chloride or Vinyl Termination

The technique used has been described by J. B. Brzoska et al., (1994), Langmuir 10, 4367.

A solution of TCSUC ($10^{-3}$ mol/l) was prepared in a hexane/$CH_2Cl_2$ solution (70/30 v/v) which was cooled to 0° C. in argon. The surfaces were brought into contact with this solution for 1 hour 30 minutes. They were then rinsed for 5 minutes in an ultrasound bath containing chloroform. Finally, they were dried in a stream of nitrogen.

IIc. Optional Modification of the Capture Layer to Obtain Carboxyl Functions (—COOH)

The silanised surfaces were immersed in a 5% aqueous $Na_2CO_3$ solution for 2×24 hours. After neutralising as above, the surfaces were rinsed with distilled water then dried in nitrogen.

IId. Grafting the Bio-active Molecule

Surface functionalised with carboxyl groups (—COOH):

A $CHCl_3$ or $CH_2Cl_2$ solution containing the following was prepared: $10^{-2}$ mol/l of APATEA and $10^{-2}$ mol/l of TEA. After dissolving, $10^{-2}$ mol/l of dicyclohexylcarbodiimide and $2×10^{-3}$ mol/l of N,N-dimethylaminopyridine were added. The surfaces were immersed in this solution and the mixture was stirred for 24 hours. The treated surfaces were rinsed with chloroform and dried.

Surface functionalised with acid chloride groups (—COCl):

The surfaces were immersed in a $CHCl_3$ solution containing $10^{-2}$ mol/l of HEDMDA and $10^{-2}$ mol/l of TEA. After stirring (24 hours), the surfaces were rinsed with chloroform and dried.

III. Preparation of Organic Surfaces

All of the organic materials used could be cleaned by immersing in an ethanolic solution stirred ultrasonically for 5 minutes.

IIIa. Polyvinyl Chloride (PVC)

The surface of polyvinyl chloride (PVC) must be activated by transforming the chloride groups into amine groups.

To this end, the PVC was immersed in an aqueous $10^{-2}$ mol/l sodium azide solution. After stirring for 24 hours at 40° C., the PVC was washed with water. It was then immersed in an aqueous $10^{-2}$ mol/l $NaBH_4$ solution for 24 hours, at 40° C.

The antibiotic could be grafted in two ways:
1) After rinsing with water, the PVC was immersed in an aqueous 5% v/v glutaraldehyde solution. It was stirred for 20 hours, $NaBH_4$ ($10^{-2}$ M) was added and stirring was continued for 4 hours, then the PVC was rinsed with water. The PVC was then immersed in an aqueous solution of 2-bromoethylamine ($10^{-2}$ M) and sodium hydroxide ($10^{-2}$ M). It was stirred for 20 hours, $NaBH_4$ ($10^{-2}$ M) was added and stirring was continued for 4 hours. After rinsing with water, the PVC was immersed in a methanol/water (75/25 v/v) solution containing N,N-dimethyldodecylamine ($10^{-2}$ M). It was stirred for 24 hours, then the PVC was rinsed with water and dried.
2) After rinsing with water, the PVC was immersed in an aqueous BPDMDA solution ($10^{-2}$ M). It was stirred for 24 hours at 40° C., then the PVC was rinsed with water and dried.

This second method preserved the integrality of the PVC (physical characteristic and chemical composition) during treatment of a finished object.

IIIb PET (Polyethylene Terephthalate)

As in the case of PVC, the PET surface must be activated by incorporating aminoalkylsilane molecules into the polymer chains. To this end, the method described by L. N. Bui et al., (1993), Analyst, 118: 463 was used.

The PET was immersed in a 2% v/v solution of 3-aminopropyltriethoxysilane in toluene for 24 hours in argon. After rinsing with chloroform and toluene, the activated PET was either immersed in a 3% v/v solution of sebacoyl chloride in toluene containing a few drops of pyridine, or in an aqueous 5% v/v glutaraldehyde solution, and then stirred for 24 hours in argon. The PET was then rinsed with toluene (in the case of an acid chloride) or with water (in the case of an aldehyde) then with ethanol. This procedure fixed spacer molecules onto the PET surface.

The acid chloride terminal functions of the spacer molecules could optionally be transformed into carboxyl groups for the mineral surfaces.

The antibiotic or bactericide was then grafted using the same procedure as that given for the mineral surfaces.

BACTERIOLOGICAL TESTS

I. Protocol

Firstly, a solution of nutrient medium containing a white staphylococcus strain (staphylococcus epidermis) (SB) was prepared in a concentration of the order of $10^5$–$10^6$ bacteria/ml.

The surfaces were tested in a quasi-static situation by immersing them in an SB solution (without stirring). The incubation period was generally 24 hours and the temperature was 37.5° C.

Different types of surface were used:
powder (spherical particles with a diameter of less than one mm);
beads (spherical particles with a diameter of over one mm);
tubes, thin films or thick plates;
fibres.

II. Results

The concentration of bacteria in the solution after incubation with the treated surfaces was determined by measuring the optical density at 600 nm, counting in a Petri dish and/or laser counting.

The results obtained for different materials are shown in the tables below.

T represents the incubation temperature, in °C.

t represents the incubation time of the solution, in hours.

$[SB]_0$ represents the number of bacteria per ml in the solution at the start time, t=0.

$[SB]_t$ represents the number of bacteria per ml in the solution after incubation for a time t.

II-1. Sand (99% silica, $SiO_2$)

| Type | Antibiotic | T (° C.) | t (h) | $[SB]_0$ | $[SB]_t$ | N° |
|---|---|---|---|---|---|---|
| Powder | none | 37.5 | 24 | $10^6$ | $250.10^6$ | A1 |
| (diameter: | APATEA | 37.5 | 24 | $10^6$ | $40.10^6$ | A2 |
| 200 μm) | HEDMDA | 37.5 | 24 | $10^6$ | <100 | A3 |

II-2. Glass (borosilicate containing 60% silica)

| Type | Antibiotic | T (° C.) | t (h) | $[SB]_0$ | $[SB]_t$ | N° |
|---|---|---|---|---|---|---|
| Beads | none | 37.5 | 24 | $10^6$ | $350.10^6$ | B4 |
| (diameter: | APATEA | 37.5 | 24 | $10^6$ | $230.10^6$ | B5 |
| 2 mm) | HEDMDA | | | | | B6 |
| Fibres | none | 37.5 | 48 | $2.10^4$ | $250.10^6$ | B7 |
| (diameter: | APATEA | | | | | B8 |
| 30 μm) | HEDMDA | 37.5 | 48 | $2.10^4$ | $40.10^6$ | B9 |
| Tube | none | | | | | B10 |
| | APATEA | | | | | B11 |
| | HEDMDA | | | | | B12 |

II-3. PVC

| Type | Antibiotic | T (° C.) | t (h) | $[SB]_0$ | $[SB]_t$ | N° |
|---|---|---|---|---|---|---|
| Powder | none | 37.5 | 24 | $10^5$ | $8.10^7$ | D1 |
| | APATEA | | | | | D2 |
| | HEDMDA | 37.5 | 24 | $10^5$ | <100 | D3 |
| Ground | none | | | $10^5$ | $6.10^7$ | D4 |
| (diameter: | APATEA | | | | | D5 |
| 3 mm) | HEDMDA | | | $10^5$ | <100 | D6 |
| Tube | none | 37.5 | 24 | $10^5$ | $7.10^8$ | D10 |
| | APATEA | | | | | D11 |
| | HEDMDA | 37.5 | 24 | $10^5$ | <20 | D12 |

II-5. PET

| Type | Antibiotic | T (° C.) | t (h) | $[SB]_0$ | $[SB]_t$ | N° |
|---|---|---|---|---|---|---|
| Powder | none | 37.5 | 24 | $10^4$ | $4.10^7$ | E1 |
| | APATEA | | | | | E2 |
| | HEDMDA | 37.5 | 24 | $10^4$ | $10^2$ | E3 |
| Fibres | none | | | | | E4 |
| | APATEA | | | | | E5 |
| | HEDMDA | | | | | E6 |
| Film | none | | | | | E10 |
| (thickness: | APATEA | | | | | E11 |
| 0.35 mm) | HEDMDA | | | | | E12 |

III. Analysis of Results

An examination of the tables shows a very clear bactericidal or bacteriostatic effect in the case of the treated surfaces. The final concentration of bacteria in a solution brought into contact with the grafted antibiotics was generally zero or not measurable under the conditions used while the final concentration measured in the absence of antibiotics increased to 1000 times more than the initial concentration, the conditions otherwise being equal.

This effect was present for all types of surfaces and for all of the materials studied.

It can be seen that the effect is greater as the specific surface area increases (large number of antibiotic or bactericidal sites) (compare, for example, cases A2 and B5).

The bactericidal efficacy of the treated surfaces appears to be exceptionally high. In a volume of 1 ml into which a 2 $cm^2$ treated surface had been immersed, it was observed that all of the bacteria had been destroyed in 24 hours while an equivalent number of bactericidal molecules taken directly into solution was ineffective. A calculation also showed that the concentration reached in this case (<1 μg/ml) was less than the CMB of the antibiotic.

The CMB values measured for these antibiotics in solution were 64 μg/ml and 4 μg/ml respectively for APATEA and HEDMDA (or BPDMDA).

In summary, the advantages of the surfaces of the invention are as follows:

chemical grafting renders the bactericidal surface treatment permanent and irreversible;

the possibility of accidental release of the organic molecules used into the surrounding medium is practically zero because of the covalent bonds with the substrate;

since the layer of organic molecules is a monolayer, a very small quantity of active product is sufficient to completely coat the surfaces to be treated;

the local concentration of bio-active molecules is very high, typically ten thousand times higher than the usual doses in solution, which endows the treated surfaces with exceptional bacteriological efficacy;

the interaction between the treated surface and the bacteria to be destroyed is based on very general physico-chemical principles rather than on specific interactions. A single coating is thus active for a number of classes of bacteria and yeasts;

the molecules used are not antibiotics and thus do not cause any microbial ecological problems;

it is possible to deposit "cocktails" of antibacterial molecules onto a single surface to broaden the spectrum;

there is no "consumption", and thus the antibacterial products deposited do not become exhausted;

the location of the antibacterial agents on the surfaces prevents the formation of biofilms and the development of bacterial colonies;

the treated objects are self-sterilised and do not demand particular storage conditions;

the surface treatment is extremely resistant. The treated materials can be washed with any of the usual solvents, they can be heated to high temperatures (120° C.), or they can be sterilised with ethylene oxide. Conventional sterilisation or decontamination is thus possible;

the chemical treatments chosen only modify the treated polymers on an atomic scale; neither the structural properties of the polymers nor their external appearance is affected;

the treated objects can have any shape or dimensions. For hollow tubes, the internal cross section and the external cross section can be coated in one and the same step. Similarly, the surfaces do not need to be flat or smooth.

What is claimed is:

1. A surface provided with antibiotic or antiseptic properties, comprising a solid substrate modified by covalently fixing one or more spacers having reactive extremities via a proximate reactive extremity, and one or more antibiotic, bactericidal, viricidal or fungicidal molecules covalently bonded to a distal reactive extremity of said spacer or spacers, said spacer having formula $$A_1-(CH_2)_n-A_2,$$

where:

$A_1$ is $$\overset{O}{\underset{\|}{C}}-Z$$

where Z=H, OH or Cl; or $SiY_3$ where $Y_3$ is Cl or an alkoxy group containing 1 to 3 carbon atoms;

n is in the range 2 to 18;

$A_2$ is selected from the following residues: $CH=CH_2$, OH, halogen or $$\overset{O}{\underset{\|}{C}}-Z,$$

where Z=H, OH or Cl.

2. The surface according to claim 1, wherein n is in the range 5 to 18.

3. The surface according to claim 1, wherein the bound molecule is an antibiotic selected from the group consisting of penicillin, cephalosporin, monobactam, thienamycin, β-lactamase inhibitor, peptidoglycan synthesis inhibitor, bacitracin and novobiocin.

4. The surface according to claim 1, wherein the bound molecule is a quaternary ammonium compound having bactericidal properties.

5. The surface according to claim 1, comprising a density of active antibiotic sites per unit surface area in the range $10^{11}$ to $5 \times 10^{14}$ molecules of antibiotics per $cm^2$.

6. The surface according to claim 1, comprising at least one additional antibiotic grafted to said surface, on which it forms a monolayer with a thickness of less than 4 mm.

* * * * *